(12) United States Patent
Kurtz et al.

(10) Patent No.: US 7,887,532 B2
(45) Date of Patent: Feb. 15, 2011

(54) SYSTEM AND METHOD FOR RESECTING CORNEAL TISSUE USING NON-CONTINUOUS INITIAL INCISIONS

(75) Inventors: Ronald M. Kurtz, Irvine, CA (US); Francis W. Price, Jr., Indianapolis, IN (US); Melvin Sarayba, Ladera Ranch, CA (US)

(73) Assignee: AMO Development, LLC., Santa Ana, CA (US)

( * ) Notice: Subject to any disclaimer, the term of this patent is extended or adjusted under 35 U.S.C. 154(b) by 1064 days.

(21) Appl. No.: 11/469,902

(22) Filed: Sep. 5, 2006

(65) Prior Publication Data

US 2008/0058777 A1   Mar. 6, 2008

(51) Int. Cl.
*A61B 18/20* (2006.01)

(52) U.S. Cl. .............................. 606/5; 606/10; 606/166; 128/898

(58) Field of Classification Search ................. 606/4–6, 606/166, 10–12; 607/88, 89; 128/898
See application file for complete search history.

(56) References Cited

U.S. PATENT DOCUMENTS

| | | | | |
|---|---|---|---|---|
| 4,764,930 A | | 8/1988 | Bille et al. | |
| 4,941,093 A | * | 7/1990 | Marshall et al. | 606/5 |
| 5,549,632 A | | 8/1996 | Lai | |
| 5,984,914 A | * | 11/1999 | Cumming | 606/4 |
| 5,984,916 A | | 11/1999 | Lai | |
| 6,004,313 A | * | 12/1999 | Shimmick et al. | 606/5 |
| 6,063,073 A | * | 5/2000 | Peyman | 606/5 |
| 6,217,571 B1 | | 4/2001 | Peyman | |
| 6,302,877 B1 | * | 10/2001 | Ruiz | 606/5 |
| RE37,585 E | | 3/2002 | Mourou et al. | |
| 6,458,141 B1 | * | 10/2002 | Peyman | 606/166 |
| 6,551,306 B1 | * | 4/2003 | Carriazo | 606/5 |
| 6,863,667 B2 | | 3/2005 | Webb et al. | |
| 6,913,603 B2 | * | 7/2005 | Knopp et al. | 606/10 |
| 6,989,008 B2 | * | 1/2006 | Peyman | 606/5 |
| 7,351,241 B2 | | 4/2008 | Bendett et al. | |
| 7,402,159 B2 | * | 7/2008 | Loesel et al. | 606/10 |
| 2002/0138069 A1 | | 9/2002 | Peyman | |
| 2003/0078607 A1 | * | 4/2003 | Carriazo | 606/166 |
| 2007/0093796 A1 | | 4/2007 | Raksi et al. | |
| 2007/0106285 A1 | | 5/2007 | Raksi | |

OTHER PUBLICATIONS

International Search Report and Written Opinion of PCT Application No. PCT/US/2007/076810, dated Apr. 1, 2008, 7 pages total.

Heisterkamp et al., "Optimierung der Laserparameter für die intrastromale Schnittführung mittels ultrakurzer Laserpulse," [Optimizing laser parameters for intrastromal incision with ultra-short laser pulses] [Article in German], Ophthalmologe. 2001 Jul. 98(7):623-628.

(Continued)

*Primary Examiner*—Ahmed M Farah

(57) ABSTRACT

A system and method for resecting corneal tissue is disclosed. A resection pattern is selected for resecting corneal tissue. The resection pattern is incised in a cornea using a surgical laser, leaving one or more uncut gaps in the incised resection pattern. Any uncut gaps left in the resection pattern may thereafter be incised using an alternate surgical instrument.

21 Claims, 5 Drawing Sheets

OTHER PUBLICATIONS

Viestenz et al., "Einfluss der Er:YAG-Laserstrahlführung auf die Schnittqualität der nichtmechanischen Hornhauttrepanation für die perforierende Keratoplastik," [Impact of an Er:YAG laser beam control on cut quality of non-mechanical corneal trepanation for penetrating keratoplasty] [Article in German], Ophthalmologe. 2003 Jun.;100(6):471-475.

Extended European Search Report of EP Application No. 07841362.2, mailed Aug. 31, 2010, 8 pages total.

* cited by examiner

SYSTEM AND METHOD FOR RESECTING CORNEAL TISSUE USING NON-CONTINUOUS INITIAL INCISIONS

BACKGROUND OF THE INVENTION

1. Field of the Invention

The field of the present invention is systems and techniques for transplanting corneas.

2. Background

The traditional technique used for performing a penetrating keratoplasty involves creating a full thickness cylindrical cut in both the recipient and donor corneas to resect corneal tissue. The resected donor tissue is then grafted into the recipient cornea, with the graft generally taking place in the same operating room and within minutes of the resection.

The advent of the femtosecond surgical laser has already significantly changed the this traditional technique. The laser, unlike manual instruments, can be used to create full thickness corneal incisions, particularly by making intrastromal cuts in tissue that was previously inaccessible to manual instruments, thereby resecting corneal tissue for transplantation. One drawback of using the femtosecond surgical laser is that it can take up valuable space within the operating room. As an alternative, the femtosecond surgical laser could be placed in a surgical preparation room, but then extreme care must be taken not to expose the internal tissues of the cornea to contaminants during the process of transferring the recipient and the donor tissue to the operating room for completion of the procedure.

Transfer of the donor tissue is not a significant challenge, as the tissue may be placed in a sealed container for transfer. Transfer of the recipient, however, poses a greater challenge.

SUMMARY OF THE INVENTION

The present invention is directed toward a system and method for resecting corneal tissue, both using non-continuous initial incisions. In the system, a surgical laser emits a pulsed laser beam which is directed into the cornea by a focusing assembly. An interface provides a plurality of incision patterns for selection of a resection pattern and selection of an uncut gap configuration within the resection pattern. The resection pattern and the uncut gap configuration are received by a controller which employs the focusing assembly to move the focal point of the pulsed laser beam and incise corneal tissue according to the resection pattern. Prior to or during the incision process, the uncut gap configuration is applied to the resection pattern such that the pulsed laser beam skips portions of the resection pattern.

In the method, a resection pattern is incised in the cornea using a surgical laser, with at least one uncut gap being left in the incised resection pattern. Afterward, any uncut gaps left in the resection pattern are incised using an alternate surgical instrument. The alternate surgical instrument may be a bladed instrument, or if the uncut gap is sufficiently small, a more blunt instrument may be employed.

Accordingly, an improved system and method for resecting corneal tissue using non-continuous initial incisions are disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1A:
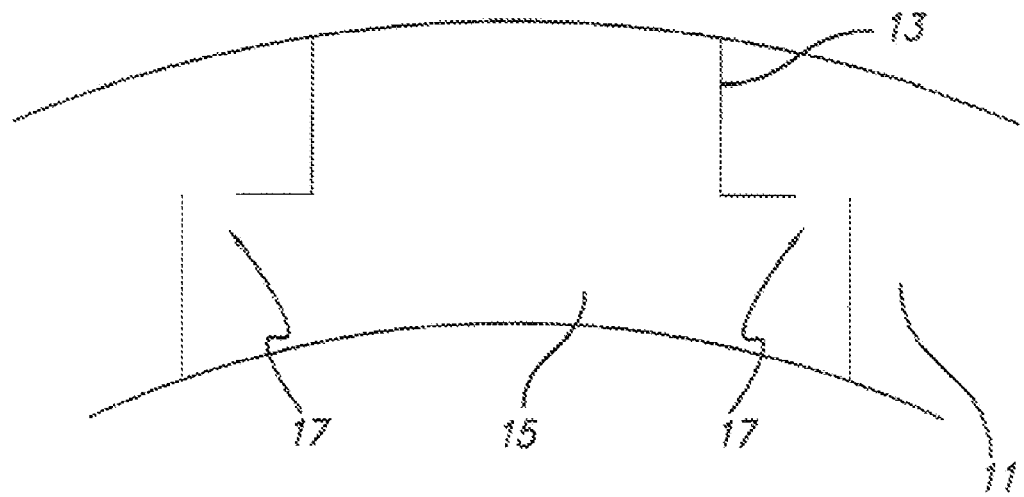
FIGS. 1A-H illustrate sectional views of corneas, each overlaid with a resection pattern which includes uncut gaps.

Turning in detail to the drawings, FIG. 1A shows the recipient cornea 11 with the profile of the resection pattern 13 overlaid. Such a resection pattern, as with all the resection patterns disclosed herein, are designed to excise corneal tissue 15 from the recipient cornea 11 as part of a corneal transplant procedure. When the cornea 11 is incised with the full resection pattern 13, without any uncut gaps, the corneal tissue 15 bounded by the resection pattern is excised from the cornea 11. However, two uncut gaps 17 are included in the resection pattern 12 shown, so that connecting tissue will continue to secure the corneal tissue 15 to the outer portion of the cornea 11 until such time as that connecting tissue is severed. The overall size of each uncut gap within the resection pattern 13 is left to the discretion of the attending surgeon. The particular location of each uncut gap 17 within the resection pattern 13 is also left to the discretion of the attending surgeon. While two uncut gaps 17 are shown, any number of uncut gaps may be left in the resection pattern, with the number of uncut gaps being at the discretion of the attending surgeon.

By leaving the uncut gaps 17 in the resection pattern 13, tissue along the incision and the internal chambers of the eye remain protected and unexposed to environmental contaminants so long as the corneal tissue 15 remains in place. The patient may therefore be moved between a preparation room, where a resection pattern having uncut gaps is incised, and an operating room, where the transplant procedure takes place, without exposing the patient to risk of the corneal tissue 15 dislodging during the move. Such risk would always be present if the entire resection pattern is incised in a preparation room prior to moving the patient to the operating room.

Once in the operating room, the uncut gaps 17 may be incised using any appropriate surgical instrument. Preferably, a bladed instrument would be used. However, if the uncut gaps are sufficiently small, they could be cut with a more blunt instrument.

Figure 1B:
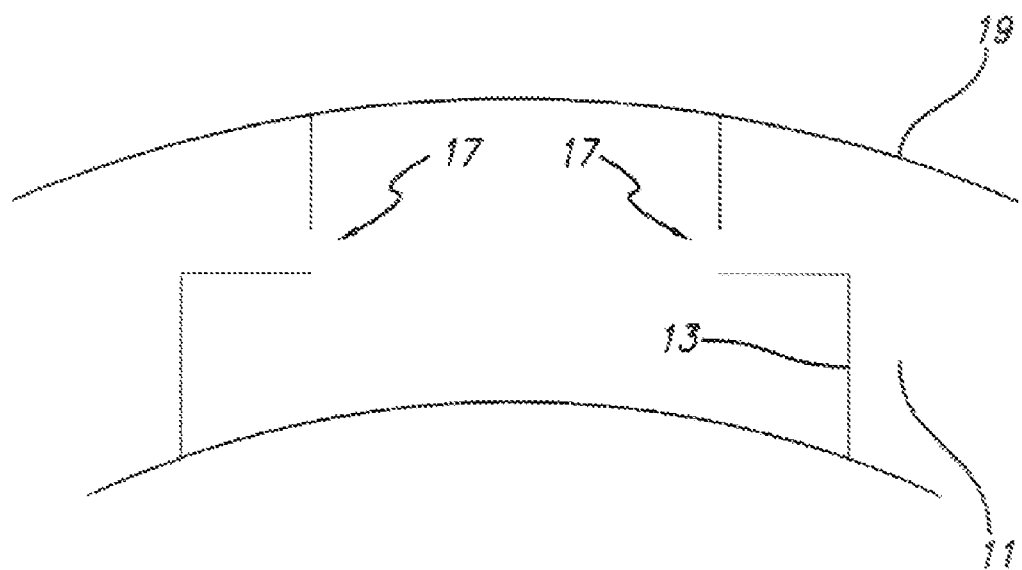
Figure 1C:
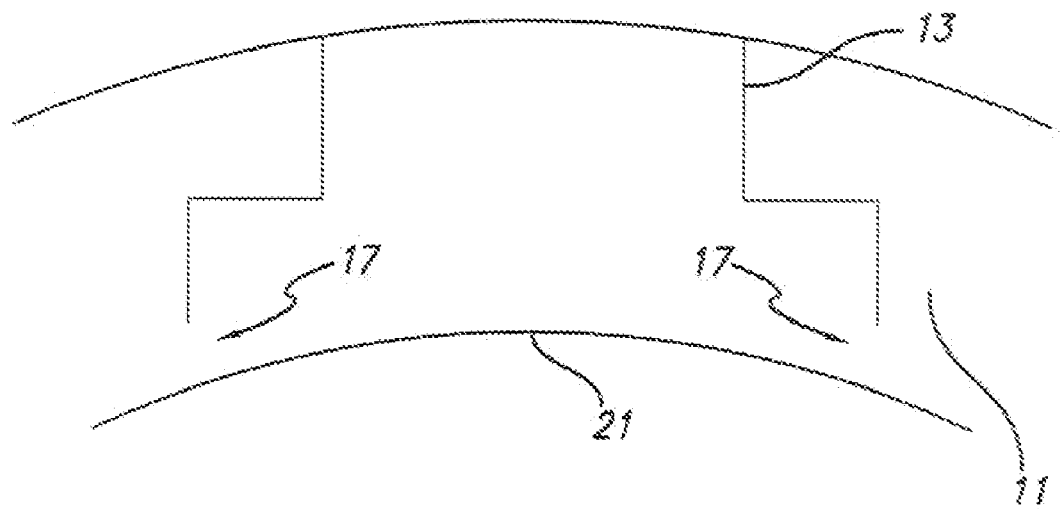

FIGS. 1B & 1C show the same resection pattern 13 overlaid on the cornea 11, but with the uncut gaps in different locations. In FIG. 1B, each uncut gap 17 is adjacent the intersection between two sections of the resection pattern 13, which come together at an angle. The uncut gaps 17 are actually disposed on the section of the resection pattern 13 running from the anterior corneal surface 19. In FIG. 1C, each uncut gap 17 is adjacent the posterior corneal surface 21.

Figure 1D:
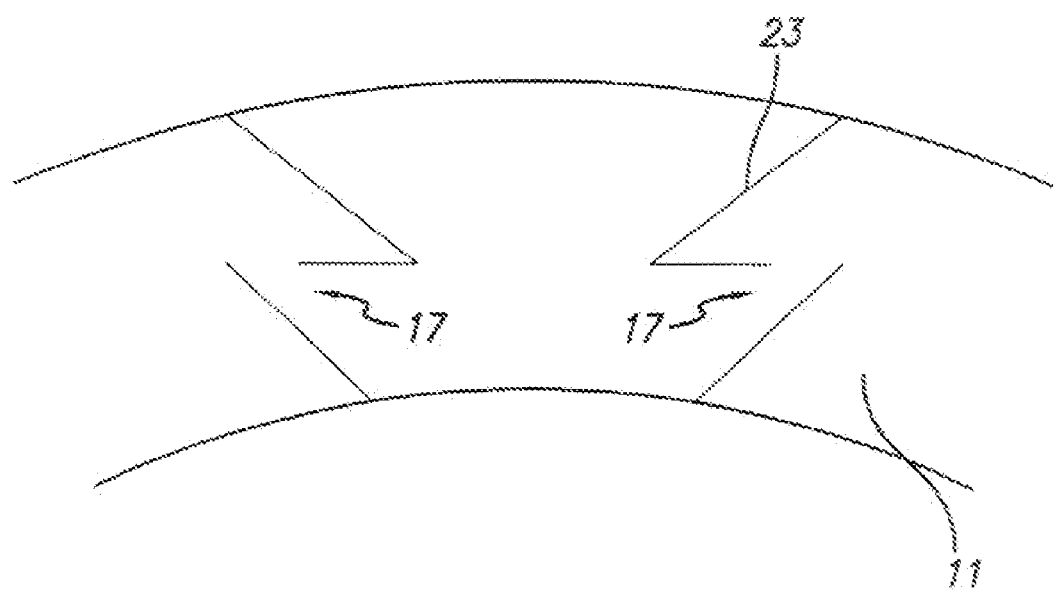
Figure 1E:
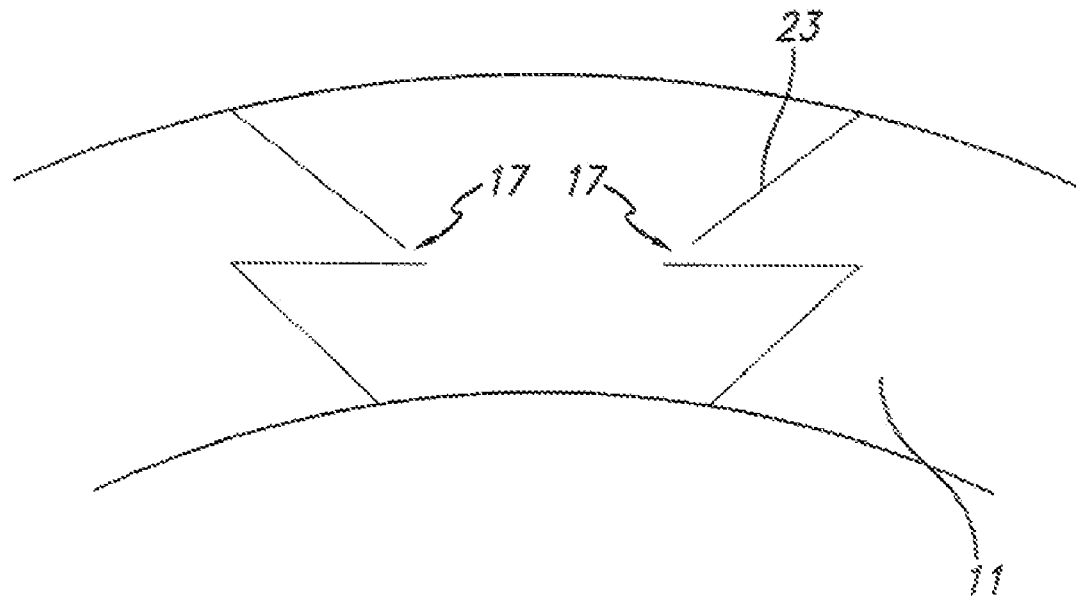
Figure 1F:
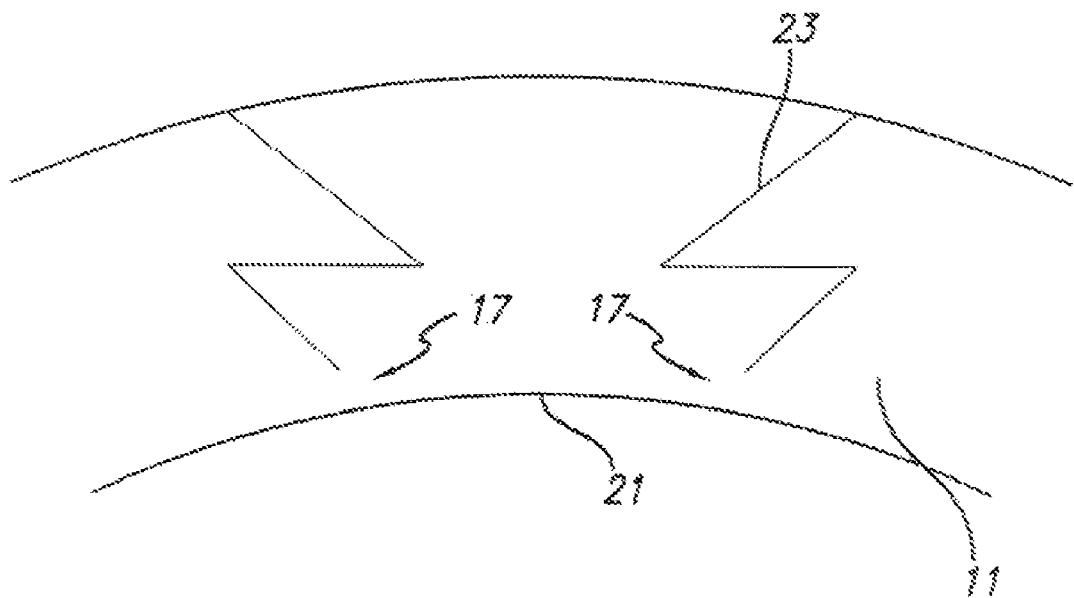

FIGS. 1D-1E each shows a resection pattern 23 which has a zig-zag pattern in profile. Again, the uncut gaps 17 may be placed at any desired location within the resection pattern 23.

Figure 1G:
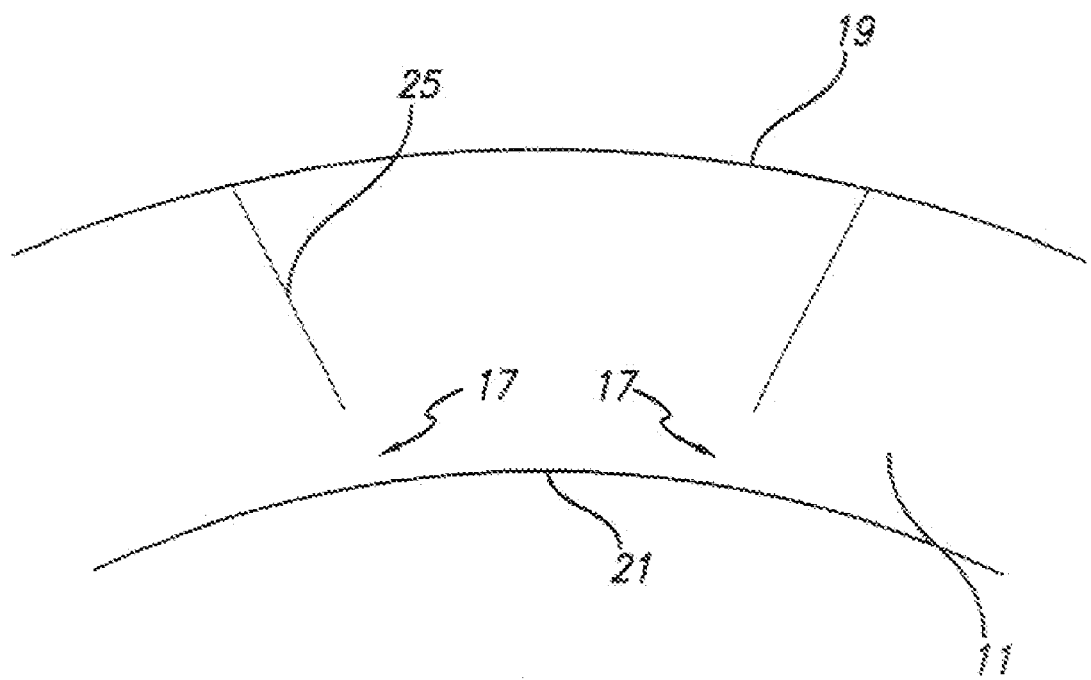
Figure 1H:
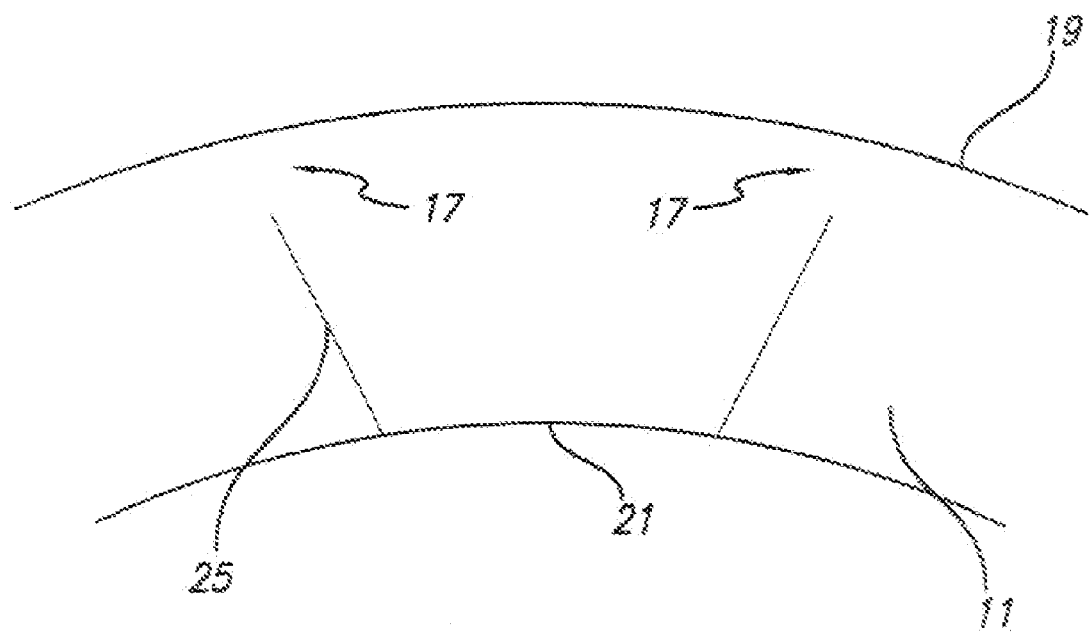

FIGS. 1G & 1H each show a resection pattern 25 which has a profile forming a straight line between the anterior corneal surface 19 and the posterior corneal surface 21. In FIG. 1G, the uncut gaps 17 are disposed at the posterior corneal surface 21, whereas the uncut gaps 17 in FIG. 1H are disposed at the anterior corneal surface 19.

Figure 2:
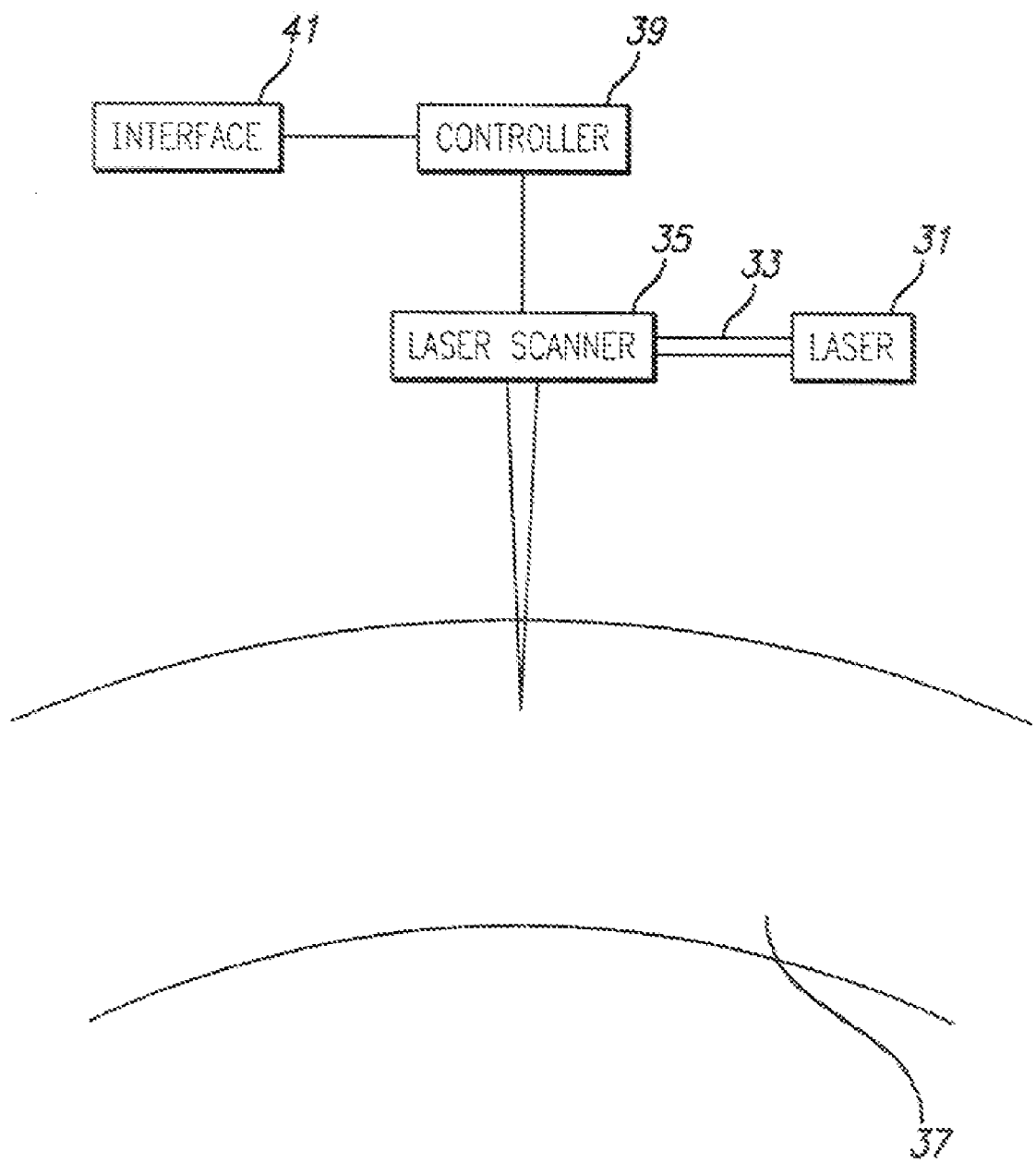
FIG. 2 schematically illustrates a system for resecting corneal tissue using a resection pattern having an uncut gap.

Referring to FIG. 2, a femtosecond surgical laser 31 generates a pulsed laser beam 33 and directs that beam into the focusing assembly 35, which in turn focuses the pulsed beam 33 into the cornea 37. The controller 39 is a programmable computer which precisely controls the location of the beam focal point within the cornea 37 according to parameters received from the surgeon interface 41. The interface 41 presents the surgeon with several incision patterns from which the desired resection pattern is selected. In addition, the interface 41 presents the surgeon with several options for gap placement from which the surgeon selects the desired gap configuration. The selected options are sent to the controller, and the controller 39 applies the selected gap configuration to the selected resection pattern for purposes of controlling the focusing assembly and incising the resection pattern, with the appropriate gaps, in the cornea. Alternatively, the controller 39 may control the beam 33 emitted from the surgical laser 31 such that the beam 33 would not be emitted as the focusing assembly 35 effectively "scans" the focal point over those parts of the resection pattern where a gap has been located. This alternative technique could be used to maintain the continuity of a pre-established scan pattern.

The surgical laser may be of the type described in U.S. Pat. No. 4,764,930, producing an ultra-short pulsed beam as described in one or both of U.S. Pat. No. 5,984,916 and U.S. Pat. No. RE37,585 to photodisrupt corneal tissues. The focusing assembly may be of the type described in U.S. patent application Ser. No. 11/272,571. The disclosures of the aforementioned patents are incorporated herein by reference in their entirety. Commercial laser systems capable of performing the incisions are available from IntraLase Corp. of Irvine, Calif.

The surgical laser may be used in conjunction with a contact lens (not shown) which is applied to the anterior corneal surface to deform the cornea. Deformation of the cornea in this manner provides multiple advantages which are well known to skilled artisans. For example, U.S. Pat. No. 5,549,632, which is incorporated herein by reference, describes advantages gained in making laser incisions by deforming the shape of the cornea, particularly by application. U.S. Pat. No. 6,863,667 and U.S. patent application Ser. No. 11/258,399, both of which are incorporated herein by reference, describe patient interface devices which deform the cornea and are used to align the surgical laser with the recipient cornea for purposes of making accurate incisions.

Thus, a system and method for resecting corneal tissue using non-continuous initial incisions are disclosed. While embodiments of this invention have been shown and described, it will be apparent to those skilled in the art that many more modifications are possible without departing from the inventive concepts herein. For example, while the embodiments described relate to a full thickness corneal transplant, the techniques and system are easily adapted for application in a lamellar corneal transplant procedure. Other applications are also possible. The invention, therefore, is not to be restricted except in the spirit of the following claims.

What is claimed is:

1. A system for resecting corneal tissue for use on a patient in preparation for a corneal transplant procedure, wherein an operating room is configured for the corneal transplant procedure, the system comprising:
    a surgical laser adapted to emit a pulsed laser beam;
    a focusing assembly adapted to focus the pulsed laser beam into a cornea;
    an interface having a plurality of alternatively selectable incision patterns so as to define a selected resected pattern including a gap placement options with an uncut gap configuration within the resection pattern; and
    a controller in communication with the interface to receive the resection pattern and uncut gap configuration, the controller being adapted to move a focal point of the pulsed laser beam within the cornea using the focusing assembly, direct the focal point of the pulsed laser beam to incise corneal tissue according to the resection pattern, and apply the uncut gap configuration to the resection pattern to skip portions of the resection pattern;
    wherein the surgical laser is disposed in a preparation room separate from the operating room, and wherein the uncut gap configuration is sufficient to inhibit inadvertent dislodging of the incised corneal tissue during repositioning of the patient from the preparation room to the operating room.

2. The system of claim 1 wherein the interface transmits the resection pattern placing at least one uncut gap at an anterior corneal surface.

3. The system of claim 1 wherein the interface transmits the resection pattern placing at least one uncut gap at a posterior corneal surface.

4. The system of claim 1 wherein the interface transmits the resection pattern placing at least one uncut gap within stromal tissue.

5. A method of resecting corneal tissue of a patient, the method comprising:
    focusing a pulsed laser beam into a corneal tissue;
    incising a resection pattern in the corneal tissue by scanning the focused laser beam inside the corneal tissue so as to define a plurality of uncut gaps in the incised resection pattern;
    incising the uncut gaps defined by the focused laser beam using an alternate surgical instrument; and
    moving the patient between the incising of the resection pattern and the incising of the uncut gaps so that the uncut gaps inhibit exposure of the incised corneal tissue during the move.

6. The method of claim 5, wherein incising the resection pattern includes incising the resection pattern in a surgical preparation location, and incising the uncut gaps includes incising the uncut gaps in a different location.

7. The method of claim 5, wherein the uncut gaps are disposed at an anterior corneal surface.

8. The method of claim 5, wherein the uncut gaps are disposed at a posterior corneal surface.

9. The method of claim 5, wherein the uncut gaps are disposed within stromal tissue.

10. The method of claim 5, wherein the alternate surgical instrument comprises a blade.

11. The method of claim 5, wherein the resection pattern comprises a first section and a second section, and an intersection between the second section and the first section forms an angle.

12. The method of claim 11, wherein the uncut gaps are disposed adjacent the intersection.

13. The method of claim 5, wherein moving the patient comprises moving from a first room to a second room.

14. A method of resecting corneal tissue, the method comprising:
    defining a resection pattern;
    focusing a pulsed laser beam into a corneal tissue;
    incising the corneal tissue by scanning the focused laser beam inside the corneal tissue per the resection pattern so as to define an uncut gap in the corneal tissue; and
    incising the uncut gap using a surgical blade.

15. The method of claim 14, wherein incising the resection pattern includes incising the resection pattern in a surgical preparation location, and incising the uncut gap includes incising the uncut gap in a different location.

16. The method of claim 14, wherein the uncut gap is disposed at an anterior corneal surface.

17. The method of claim 14, wherein the uncut gap is disposed at a posterior corneal surface.

18. The method of claim 14, wherein the uncut gap is disposed within stromal tissue.

19. The method of claim 14, wherein the resection pattern comprises a first section and a second section and an intersection between the second section and the first section forms an angle.

20. The method of claim 19, wherein the uncut gap is disposed adjacent the intersection.

21. The method of claim 14 further comprising moving the patient between the incising of the resection pattern in a first room and the incising of the uncut gap in a second room.

* * * * *